US008726718B2

(12) United States Patent
Rouse

(10) Patent No.: US 8,726,718 B2
(45) Date of Patent: May 20, 2014

(54) PAYOUT-GLIDE-FLAKEOFF APPARATUS FOR CHARACTERIZING DEODORANT AND ANTIPERSPIRANT STICKS

(75) Inventor: John P. Rouse, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 836 days.

(21) Appl. No.: 12/878,725

(22) Filed: Sep. 9, 2010

(65) Prior Publication Data

US 2011/0005299 A1 Jan. 13, 2011

Related U.S. Application Data

(62) Division of application No. 11/971,978, filed on Jan. 10, 2008, now Pat. No. 7,810,372.

(60) Provisional application No. 60/976,527, filed on Oct. 1, 2007, provisional application No. 61/015,852, filed on Dec. 21, 2007.

(51) Int. Cl.
*G01N 19/00* (2006.01)
*G01N 19/02* (2006.01)
*G01N 33/00* (2006.01)

(52) U.S. Cl.
USPC ............................................ 73/9; 73/7

(58) Field of Classification Search
USPC ................................................. 73/7, 9
See application file for complete search history.

(56) References Cited

U.S. PATENT DOCUMENTS

| 3,904,805 | A | 9/1975 | Johnson et al. |
| 4,474,283 | A | 10/1984 | Solaroli |
| 5,404,751 | A | 4/1995 | Beran et al. |
| 2002/0076390 | A1 | 6/2002 | Kantner et al. |
| 2005/0081607 | A1 | 4/2005 | Patel et al. |
| 2005/0183511 | A1 | 8/2005 | Giron |
| 2005/0226820 | A1 | 10/2005 | Brown |
| 2006/0140902 | A1 | 6/2006 | MacDonald et al. |
| 2006/0174383 | A1 | 8/2006 | Huang |
| 2006/0243297 | A1 | 11/2006 | Brown |
| 2007/0166254 | A1 | 7/2007 | Bianchi |
| 2007/0212394 | A1 | 9/2007 | Reyes et al. |
| 2009/0000508 | A1 | 1/2009 | Edison et al. |

FOREIGN PATENT DOCUMENTS

| GB | 2162953 | 2/1986 |
| RU | 2110787 | 5/1998 |
| SU | 1429003 | 10/1988 |
| WO | WO 2005/037432 | 4/2005 |
| WO | WO 2005/038432 | 4/2005 |

OTHER PUBLICATIONS

Ramasubramanian, M.K., et al., A Friction Sensor for Real-Time Measurement of Friction Coefficient on Moving Flexible Surfaces, Oct. 22, 2003, Sensors, 2003. Proceedings of IEEE, vol. 1,152-157.*

(Continued)

*Primary Examiner* — Daniel S Larkin
(74) *Attorney, Agent, or Firm* — Michael F. Morgan

(57) ABSTRACT

An apparatus and system for characterizing and quantifying certain attributes of antiperspirants and deodorants is provided, such as payout, friction, and flakeoff. The apparatus is capable of reproducibly applying antiperspirants and deodorant to a substrate.

4 Claims, 5 Drawing Sheets

(56) References Cited

OTHER PUBLICATIONS

PRWEB—Online Visibility from Vocus—"Testing Machines Group New Oscillating Payout and Friction Tester from Testing Machines Inc.", Jan. 31, 2007, two pages.*

Testing Machines Inc., 32-71 Oscillating Payout & Friction Tester, http://www.testingmachines.com/32-71-oscillating-payout-friction-tester.html, one page.*

Alliston-Greiner A F: "Friction test machines for rubbery materials." TRIBOTEST. (1994) pp. 63-75. 1 :1. XP002094975. ISSN: 1354-4063.

Wada N: "Rubber Friction Test Methods," International Polymer Science and Technology. (1998) pp. T52-T59. 25:2 XP000774996 ISSN: 0307-174X.

International Search Report PCTIUS2008/051850 Date of Mailing Feb. 18, 2009.

Ramasubramanian, M.K., Jackson, Steven D., A Friction Sensor for Real-Time Measurement of Friction Coefficient on Moving Flexible Surfaces, Oct. 22, 2003, Sensors, 2003. Proceedings of IEEE, vol. 1, 152-157.

* cited by examiner

PAYOUT-GLIDE-FLAKEOFF APPARATUS FOR CHARACTERIZING DEODORANT AND ANTIPERSPIRANT STICKS

CROSS REFERENCE TO RELATED APPLICATIONS

This application is a divisional application of U.S. Ser. No. 11/971,978, filed on 10 Jan. 2008, now U.S. Pat. No. 7,810,372, which claims priority to U.S. Application Ser. Nos. 60/976,527, filed on 1 Oct. 2007 and 61/015,852, filed on 21 Dec. 2007, all of which are incorporated herein by reference.

BACKGROUND

Antiperspirant or deodorant formulations have been developed with a range of different product forms. One of these is a so-called "stick" which is usually a bar of an apparently firm solid material held within a dispensing container and which retains its structural integrity and shape whilst being applied. When a portion of the stick is drawn across the skin surface, a film of the stick composition is transferred to the skin surface. Payout, of a deodorant stick, describes the weight lost to a surface from a typical application of the deodorant stick. This attribute and other rheological properties are considerations when developing new stick deodorant products. Therefore, a controlled method and device for measuring such properties is desirable.

BRIEF SUMMARY

In an embodiment of the present invention, a system for measuring any or all of payout, static friction and kinetic friction is disclosed. The system includes at least one substrate positioned on an XYZ translational substrate bed. The system includes a sample holder for supporting a sample, wherein the sample holder and the sample are positioned perpendicular to the XYZ translational substrate bed. The system further includes a force device placing a predetermined weight onto the sample holder; the predetermined weight determines a contact force placed by the sample onto the substrate. The system also includes frictionless bearing table connected to the sample holder and a stationary frictionless bearing table positioned parallel to the XYZ translational substrate bed. The sample holder and the stationary frictionless bearing table are connected to a friction sensor. The system also includes a balance for obtaining a first substrate weight before movement of the XYZ translational substrate bed and a second substrate weight after movement of the XYZ translational substrate bed.

The system further includes a controller operably coupled to the moving substrate bed and the friction sensor and configured to execute a machine readable program code containing executable instructions.

In an embodiment of the present invention, a method for measuring payout is disclosed. The method comprises: positioning a substrate of pre-known weight on an XYZ translational substrate bed; supporting a sample in a sample holder, wherein the sample is perpendicular to the XYZ translational substrate bed; placing a predetermined weight onto the sample holder so that the sample and substrate form a contact point; first moving the XYZ translational substrate bed at a first sweep speed in a first direction relative to the sample; second moving the XYZ translational substrate bed at a second sweep speed in a second direction relative to the sample; conducting the first moving and the second moving for a predetermined number of cycle(s); obtaining a second substrate weight of the substrate after the predetermined number of cycles; and determining a payout value based on the first substrate weight and the second substrate weight.

In an embodiment of the present invention, a method for measuring one or more of static friction and kinetic friction is provided. The method comprises: positioning a substrate of pre-known weight on an XYZ translational substrate bed; supporting a sample in a sample holder, wherein the sample is perpendicular to the XYZ translational substrate bed; placing a predetermined weight onto the sample holder so that the sample and substrate form a contact point; first moving the XYZ translational substrate bed at a first sweep speed in a first direction relative to the sample; second moving the XYZ translational substrate bed at a second sweep speed in a second direction relative to the sample; conducting the first moving and the second moving for a predetermined number of cycle(s); during the first moving step and the second moving step, measuring one or more friction values at the contact point; analyzing one or more friction values generated at the sample contact point during the first moving step and the second moving step; and determining one or more of a static friction value and a kinetic friction value based on the one or more friction values.

In an embodiment of the present invention, a method for measuring flakeoff is provided. The method comprises: providing a wool sample of a predetermined size; applying an initial weight of a material to the wool sample; attaching a first end of the wool to a stationary holder and a second end to a movable substrate bed; a stretching step comprising moving the movable substrate bed a predetermined distance and returning and then moving it to an opposite direction for the same predetermined distance and returning for 1 stretch; repeating the stretch step for a predetermined number of stretches; measuring the weight of the wool sample and material after the predetermined number of stretches; determining a weight loss of material from the wool sample as measured by an amount of material lost from the sample divided by the initial weight of material after the predetermined number of stretches.

In each of the above methods, the methods are conducted on the above described system.

BRIEF DESCRIPTION OF DRAWINGS

Reference will now be made in detail to embodiments of the present disclosure, examples of which are illustrated in the accompanying drawings. Wherever possible, the same reference numbers will be used throughout the drawings to refer to the same or like parts.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a reference, the present disclosure controls.

Figure 1:
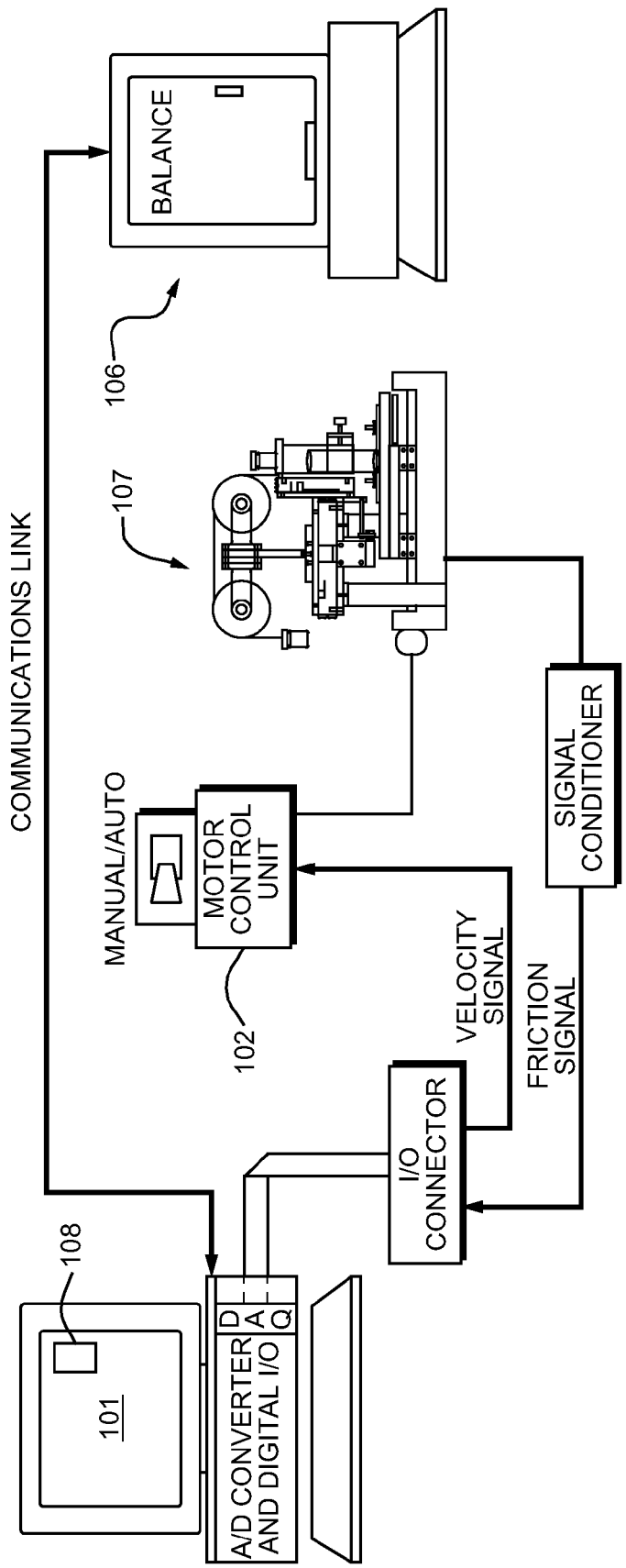
FIG. 1 illustrates an exemplary system to measure payout, static friction, kinetic friction, and combinations thereof.

The present invention provides for systems and methods for measuring payout, static friction, kinetic friction or combinations thereof. FIG. 1 illustrates an exemplary system 100 including a payout friction tester device 107, a balance 106, and a controller 101 having a machine readable program code 108 containing executable instructions. The device 107 for measuring payout, static friction, kinetic friction or combinations thereof can be operably linked to the controller 101 through a motor control unit 102. The components of the exemplary system 100 illustrated in FIG. 1 are described further below.

Figure 2:
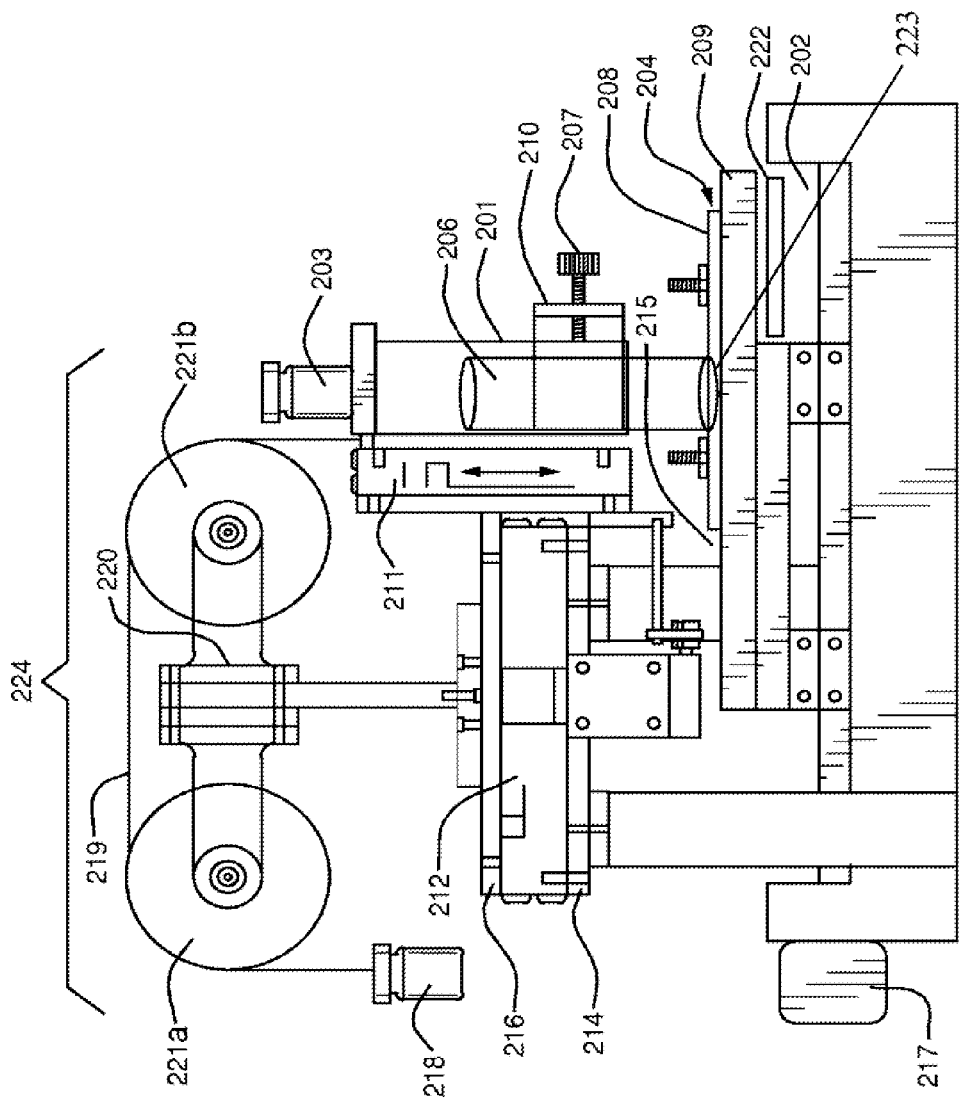
FIG. 2 illustrates an exemplary device to measure payout, static friction, kinetic friction, and combinations thereof.

FIG. 2 illustrates an exemplary payout friction device 107. Device 107, of system 100, includes: at least one substrate 204 positioned on an XYZ translational substrate bed 209; a sample holder 201; a force device 224; a frictionless bearing table 211; a stationary frictionless bearing table 212; and a friction sensor 213. Sample holder 201 supports sample 206 so that the sample 206 can be positioned perpendicular to the XYZ translational substrate bed 209 or so that the sample 206 contacts the substrate 204 perpendicularly. The sample holder 201 can also support the sample 206 such that the sample 206 contacts the substrate 204 at an angle that is less than 90°.

Sample 206 can be any sample that can be analyzed for payout, static friction, kinetic friction or combinations thereof. Examples of samples include but are not limited to deodorants (e.g. a deodorant stick), antiperspirants, or combinations thereof. The sample 206 can be secured to the sample holder 201 using a screw 207, such as a knurled thumbscrew, or other means for attachments, such as a clip or other means that can secure the sample 206 and assist in orienting its alignment. The sample clamp 210 can accept deodorant stick canisters 206 or other types of sample containers of various sizes and configurations.

Substrate 204 may include materials such as copier grade paper, sandpaper (in differing grades of abrasion) or cloth may be used. In some embodiments, it is convenient to cut the substrate beforehand in bulk, for example, into approximately 13×25 centimeter strips so that single strips can be clamped in place before testing.

Referring again to FIG. 2, the XYZ translational substrate bed 209 functions to move the XYZ translational substrate bed at a first sweep speed in a first direction and at a second sweep speed in a second direction relative to the sample 206. The XYZ translational substrate bed 209 is operably coupled to a motorized screw table 202. The motorized screw table 202 can be driven by an electronic drive unit 217. The electronic drive unit 217 can operate in an automated mode or a manual mode. In the automatic mode, the electronic drive unit 217 can include a pulse width modulation speed control so to achieve precise speed control down to a zero velocity high torque condition. The motor 103 can be remotely driven by a velocity signal furnished by the controller 101, for example by the controller's analog output channel. This allows precise control over the sweep rate and distance. In the manual mode, an operator manipulates the XYZ translational substrate bed 209 using controls of the electronic drive unit 207. An example of an electronic drive unit 217 is, but not limited to, a Motamatic Drive Unit.

In one embodiment, the XYZ translational substrate bed 209 also includes a heater 222. In some embodiments, the heater 222 is capable of heating the substrate 204 to a temperature of about 26.7° C. to about 43.3° C. (about 80° F. to about 110° F.), about 32.2° C. to about 43.3° C. (about 90° F. to about 110° F.), about 32.2° C. to about 37.8° C. (about 90° F. to about 100° F.), about 35° C. to about 37.8° C. (about 95° F. to about 100° F.), about 36.7° C. to about 37.8° C. (about 98° F. to about 100° F.), 36.7° C. to about 37.2° C. (about 98° F. to about 99° F.), or about 37° C. (about 98.6° F.).

Frictionless bearing table 211 is connected to the sample holder 201 permitting "frictionless" movement of the sample 206 supported by the sample holder 201. In some embodiments, the frictionless bearing table 211 is positioned perpendicular to the XYZ translational substrate bed 209. In other embodiments, the frictionless bearing table 211 is positioned vertically. The frictionless bearing table 211 functions to maintain an axis of pressure with testing and permits up and down movement of the sample holder 201. The weight of the sample holder 201 can be counter balanced to zero force through counterweight 218 via the pulley tower 220 and cable 219. Additional weight(s) 203 are placed on top of the sample holder 201 to define the magnitude of contact force (that which presses the sample against the surface).

A stationary frictionless bearing table 212 is positioned parallel to the XYZ translational substrate bed 209. In some embodiments, the stationary frictionless bearing table 212 is a horizontal frictionless bearing table. In other embodiments, the stationary frictionless bearing table 212 is positioned on internal rails supported by a plurality of ball bearings. The stationary frictionless bearing table floor 214 is part of the base 216 for device 107 and does not move permitting the measurement of force with respect to a solid reference.

Friction sensor 213 is operably connected to the sample holder 201 and the stationary frictionless bearing table 212. In one embodiment, friction sensor 213 can be mounted above the XYZ translational bed 209 on a bracket secured to the stationary frictionless bearing table floor 214. Lateral friction is transmitted to the friction sensor 213 through a linkage 215 coupling arrangement. This linkage 215 can be oriented as close as practical to the plane of actual friction. Measuring friction at the sample contact point 223 requires that other friction points in the machine be eliminated or at least minimized as much as possible. To accomplish this, the stationary frictionless bearing table 212 supports the upper assembly completely. All of the assembly components can be bound together on a supporting structure 216 (shown as a sideways T in black). This "rides" as one piece on the stationary frictionless bearing table 212.

Figure 3:
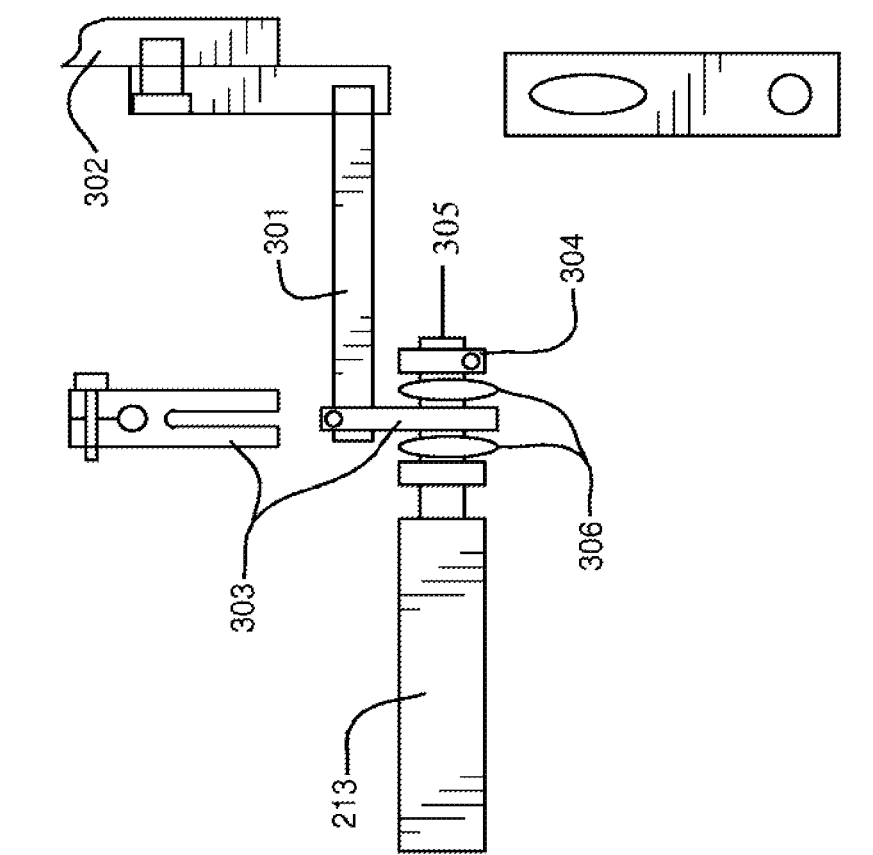
FIG. 3 illustrates an exemplary friction sensor.

The friction sensor 213 can be any sensor that can be used to detect and determine friction. Transferring surface friction to the sensing element can be done by a mechanical linkage from the sample holder 201 to the friction sensor 213. Referring to FIG. 3, the friction sensor 213 is operably coupled to a linkage 215 including a transmitter bar 301 and a linkage fork 303. Transmitter bar 301 connects registered force at the sample contact point 223 (FIG. 2) from the sample carriage mount 302 to the linkage fork 303. The linkage fork 303 can be positioned between a pair of O-ring dampeners 306 and the pair of O-ring dampeners can be positioned between a pair of element stops 304. The linkage fork 303 is suspended between two element stops 304 attached to the friction sensor probe 305. When the linkage fork 303 pushes against a stop its force content is transferred to the friction sensor 213. Physical contact at the stops is intentionally dampened by rubber "O" rings 306 which assist in smoothing out the elastic ringing that results from abrupt changes in force direction Referring again to FIG. 2, device 107 can include a force device 224 including a predetermined weight 203, a counter weight 218, a cord 219, a pulley tower 220, and two pulleys 221a and 221b. Force device 224 functions to place a predetermined weight 203 onto sample holder 201 where the predetermined weight 203 determines a contact force placed by the sample 206 onto the substrate 204. The predetermined weight 203 and the counter weight 218 can be connected by the cord 219. In some embodiments, the stationary frictionless bearing table 212 supports force device 224.

Referring to both FIG. 1 and FIG. 2, system 100 may also include a controller 101. for monitoring and controlling the desired variables. Any type of controller can be used to operate the system. Installed in the controller is a multi-functional A/D converter card (DAQ) providing the necessary interface to the system to the various components. Controller 101 is operably coupled to the XYZ translational substrate bed 209, the balance 106, and the friction sensor 213 and configured to execute the machine readable program code 108. Controller 101 is configured to execute machine readable program code 108 to perform various functions. In some embodiments, the functions include, but are not limited to configuring the balance 106 to obtain the first substrate weight before movement of the XYZ translational substrate bed 209 and the second substrate weight after movement of the XYZ translational substrate bed 209. Controller 101 also configures the XYZ translational substrate bed 209 to move the XYZ translational substrate bed 209 at a first sweep speed in a first direction and at a second sweep speed in a second direction relative to the sample 206. Controller 101 also analyzes one or more friction values, measured by the friction sensor, generated at the sample contact point 223 located between the sample 206 and the substrate 204 during movement of the XYZ translational substrate bed 209. Controller 101 is further configured to determine a static friction value and a kinetic friction value based on the one or more friction values or determine a payout value based on the first substrate weight and the second substrate weight.

Figure 5:
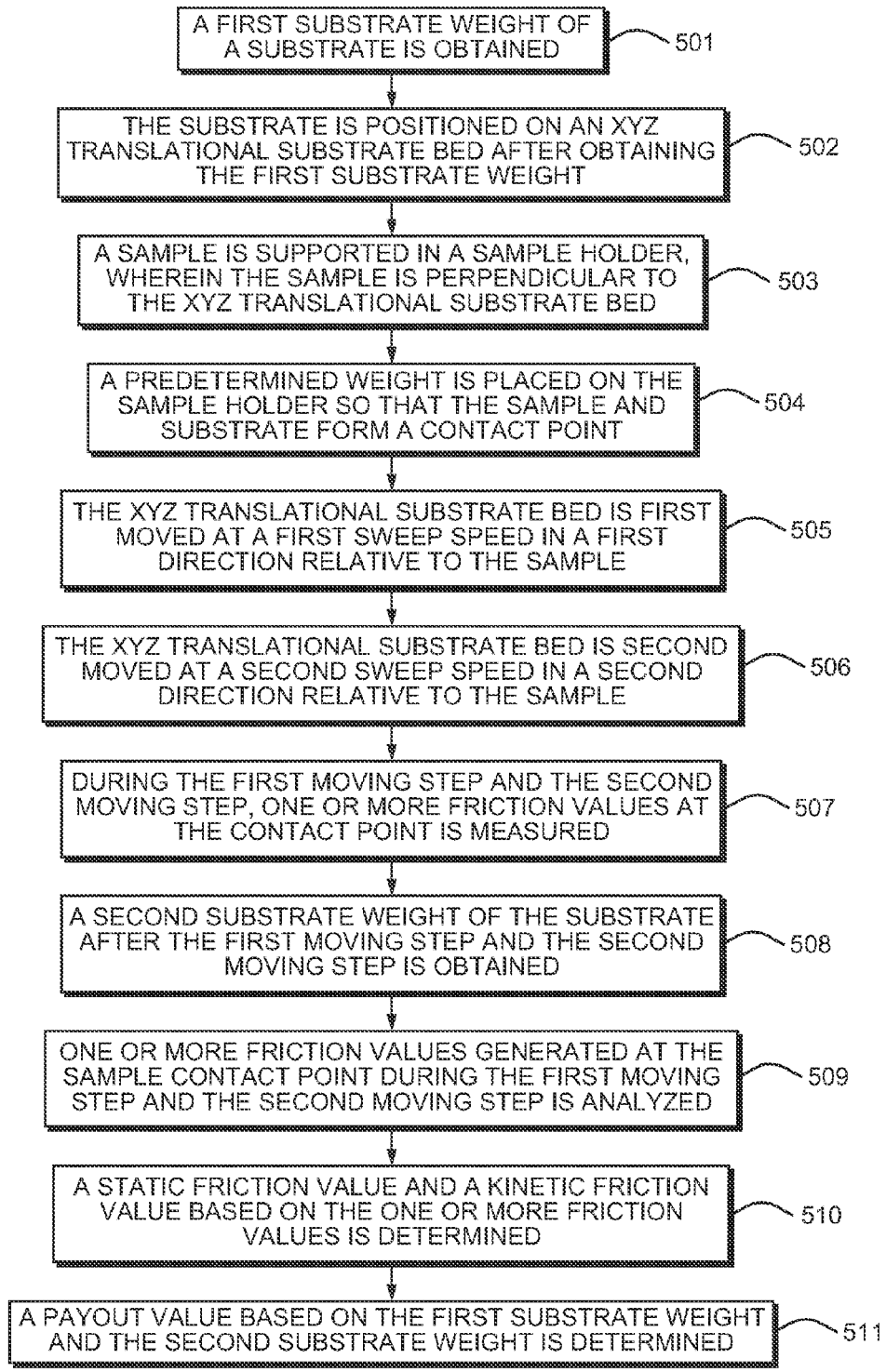
FIG. 5 illustrates an exemplary method using the systems described herein.

The system of the present invention can also be configured to execute machine readable code containing executable program instructions to perform a variety of functions. In some embodiments, the system is configured to perform methods for measuring one or more of the following: payout, static friction and kinetic friction. One embodiment for measuring one or more of the following: payout, static friction and kinetic friction is illustrated in FIG. 5. In step 501, a first substrate weight of a substrate is obtained. In one embodiment, a fresh piece of substrate 204 is placed into the balance 106 to be weighed. A continuous reading from the balance 106 is displayed in the window as the balance 106 is loaded. Once a stable reading is noted it can be "acquired" by pushing an on screen button labeled "Get weight". The substrate 204 is then removed from the balance 106 and secured to the XYZ translational bed 209 with clamping plates 208 on the longitudinal sides.

In step 502 the substrate is positioned on an XYZ translational substrate bed after obtaining the first substrate weight. In step 503 a sample is supported in a sample holder, wherein the sample is perpendicular to the XYZ translational substrate bed. In step 504 a predetermined weight is placed onto the sample holder so that the sample and substrate form a contact point.

In step 505 the XYZ translational substrate bed 209 is first moved at a first sweep speed in a first direction relative to the sample. In step 506 the XYZ translational substrate bed is second moved at a second sweep speed in a second direction relative to the sample. In one embodiment, controller 101 begins the sweeping process when permission is given by an operator. In another embodiment, controller 100 begins the sweeping process based on an automated process where permission is not needed but instead the process begins when the sample 206 and the substrate 204 are secured. The sweeping steps 505 and 506, are performed by a motorized screw table that is driven by an electronic drive unit. The electronic drive unit can have a pulse width modulation speed control. In some embodiments, the first moving step and the second moving step are repeated a predetermined number of times. In some embodiments, the first moving step and the second moving step are performed 1-50, 1-40, 1-30, 1-20, 1-10, 5-10, 5-15, 5, or 10 times.

The distance moved in the first direction or the second direction by the XYZ translational substrate bed 209, during the sweep steps 505 and 506 can be varied. In some embodiments, the distance of the first direction or the second direction is about 5 to about 50 cm, about 5 to about 40 cm, about 5 to about 30 cm, about 5 to about 20 cm, about 5 to about 10 cm. In some embodiments, distance of the first direction or the second direction is about 5, about 10, about 15, about 20, about 25, about 30, about 35, about 40, or about 50 cm.

In step 507 during the first moving step and the second moving step, one or more friction values at the contact point is measured. In some embodiments, lateral friction can be measured directly as the XYZ translational substrate bed 209 sweeps in the first and second directions. In one embodiment, each response from the friction sensor 213 can be displayed in real time at controller 101, as the sweeping continues.

In step 508 a second substrate weight of the substrate after the first moving step and the second moving step is obtained. When the requested number of sweep steps has occurred the computer can re-display the "Get weight" window. The impregnated material, i.e. substrate 204, can be removed from the lower bed and placed back into the balance 106 to be post-weighed. Payout is determined from the change in weight of the substrate 204.

In step 509 one or more friction values generated at the sample contact point during the first moving step and the second moving step is analyzed. In step 510 a static friction value and a kinetic friction value based on the one or more friction values are determined. In some embodiments the friction values are determined using the formula described herein. In step 511 a payout value based on the first substrate weight and the second substrate weight is determined.

Figure 4:
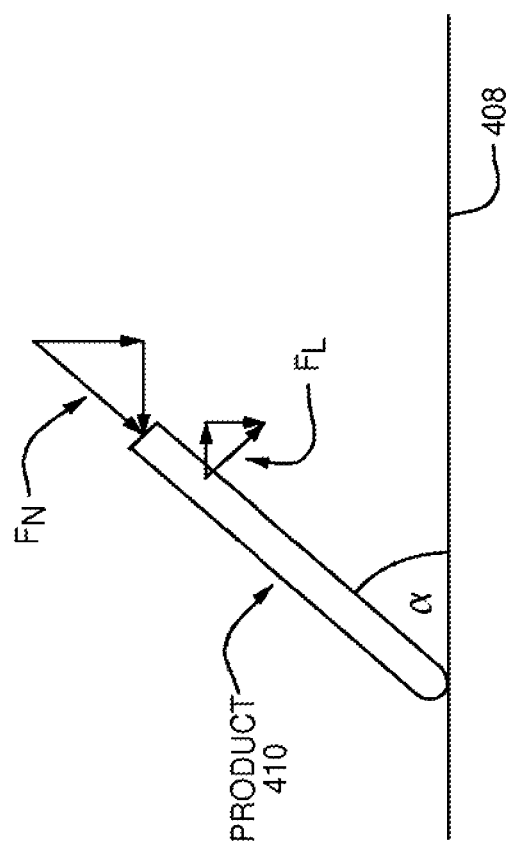
FIG. 4 illustrates a model for determining the friction coefficient.

The present invention also provides for determining friction coefficients as the substrate and sample pass against one another. Using the systems described herein the sample moves or glides across the substrate in a pattern that involves acceleration and de-acceleration unlike the previous assumption that the motion occurs with uniform speed. Therefore, the following model based on Newton's second law was employed to calculate the coefficient of friction between the sample and the substrate. FIG. 4 illustrates a model configuration of the substrate and sample passing against one another where $F_N$ is the normal force applied to the skin 408, $F_L$ is the net lateral force across the skin 408, $\alpha$ is the angle between the product 410 and the skin 408 at any given time. Based on the configuration displayed in FIG. 4, the friction coefficient at any given time can be express as following:

Driving force=$F_L \sin(\alpha) - F_N \cos(\alpha)$; Friction Force=$\mu^*[F_L \cos(\alpha) + F_N \sin(\alpha)]$; Newton's second law: $F_L \sin(\alpha) - F_N \cos(\alpha) - \mu^*[F_L \cos(\alpha) + F_N \sin(\alpha)] = m^*a$; $\mu = \{F_L \sin(\alpha) - F_N \cos(\alpha) - m^*a\} / [F_L \cos(\alpha) + F_N \sin(\alpha)]$; where $m^*a$ is the inertia of the (carriage+sample) times acceleration (a).

The device 107 can also be used to measure flakeoff. Flakeoff is a measure of weight loss of material from a sample that has been stretched. It is a measure of how well a material (such as an antiperspirant/deodorant composition) will remain on a substrate. In one embodiment, a predetermined amount of material (for example, 0.65±0.03 g) to be tested is applied onto a piece of wool (Style #530 from Testfabrics, Inc.) of a predetermined size (for example, 7.6 cm×15.2 cm (3 in.×6 in.)). The wool is stretched a predetermined distance (for example 6 cm) and returned and then stretched to the opposite direction for the same predetermined distance and returned as one stretch. The weight of the wool and material is measured after a predetermined number of stretches (for example 50, 150, and/or 450 stretches). The percent weight loss of the material from the wool is recorded as a measure of flake-off. In one embodiment, the results from four samples can be averaged to give an averaged result. In device 107, one end of the wool is attached to a stationary holder, which is attached to the frictionless bearing table 211 as replacement of sample holder 201, and the other end of the wool is attached to substrate bed 209; oriented across the 15.2 cm length. The wool is thus perpendicular to the substrate bed 209. Substrate bed 209 is then moved to stretch the wool.

EXAMPLES

Example 1

Payout/Glide on Sample

Payout on a sample is measured using the system described herein. The system holds the deodorant stick flush to the substrate and moves the stick with a set speed over a distance of 100 mm with 500 g of force. The payout program measures the amount of the product applied to a cotton substrate after ten strokes, whereas the glide program measures the friction to move the stick across the substrate during one stroke. Immediately prior to payout analysis, three sticks of each experimental stick are cut flat and then the stick surface was is further flattened or conditioned on the instrument using a speed of 30 mm/sec for twenty cycles. In order to determine the payout, the cotton substrate is tared on a balanced and then clamped down on the substrate bed. The stick is passed over the substrate ten times at a speed of 20 mm/sec, and then the substrate is removed and returned to the balance to obtain the weight of the product on the substrate. The payout is measured three times on a stick and the average of the three results is calculated. The friction coefficient for the first and tenth strokes is recorded.

What is claimed is:

1. A method for measuring one or more of static friction and kinetic friction on a system that comprises:
   at least one substrate positioned on an XYZ translational substrate bed;
   a sample holder for supporting a sample, wherein the sample holder and the sample are positioned perpendicular to the XYZ translational substrate bed;
   a force device placing a predetermined weight onto the sample holder, the predetermined weight determining a contact force placed by the sample onto the substrate;
   a frictionless bearing table connected to the sample holder;
   a stationary frictionless bearing table positioned parallel to the XYZ translational substrate bed;
   a friction sensor connected to the sample holder and the stationary frictionless bearing table;
   a balance for obtaining a first substrate weight before movement of the XYZ translational substrate bed and a second substrate weight after movement of the XYZ translational substrate bed; and
   a controller operably coupled to the XYZ translational substrate bed, the balance, and the friction sensor, the controller configured to:
   configure the balance to obtain the first substrate weight and the second substrate weight;
   configure the XYZ translational substrate bed to move the XYZ translational substrate bed at a first sweep speed in a first direction and at a second sweep speed in a second direction relative to the sample;
   analyze one or more friction values, measured by the friction sensor, generated at a sample contact point located between the sample and the substrate during movement of the XYZ translational substrate bed; and
   determine one or more of a static friction value based on the one or more friction values, a kinetic friction value based on the one or more friction values, and a payout value based on the first substrate weight and the second substrate weight,
   the method comprises:
   positioning the substrate of pre-known weight on the XYZ translational substrate bed;
   supporting the sample in the sample holder;
   placing the predetermined weight onto the sample holder so that the sample and substrate form a contact point;
   first moving the XYZ translational substrate bed at a first sweep speed in a first direction relative to the sample;
   second moving the XYZ translational substrate bed at a second sweep speed in a second direction relative to the sample;
   conducting the first moving step and the second moving step for a predetermined number of cycle(s);
   during the first moving step and the second moving step, measuring one or more friction values at the contact point;
   analyzing one or more friction values generated at the sample contact point during the first moving step and the second moving step; and
   determining one or more of a static friction value and a kinetic friction value based on the one or more friction values.

2. The method of claim 1 further comprising preconditioning the sample comprising conducting the method in claim 1 up to the conducting step for 20 cycles at a first sweep speed and second sweep speed of 30 mm/s on a substrate that is then discarded.

3. The method of claim 1, wherein the XYZ translational substrate bed is heated to a temperature of 37° C.

4. The method of claim 1, wherein the sample comprises an antiperspirant or deodorant stick.

* * * * *